United States Patent [19]

Youssef

[11] Patent Number: 4,576,190

[45] Date of Patent: Mar. 18, 1986

[54] TOOTHSTICKS "TOOSTIX"

[76] Inventor: Kamal A. Youssef, P.O. Box 6548, W. Palm Beach, Fla. 33405

[21] Appl. No.: 451,978

[22] Filed: Dec. 21, 1982

[51] Int. Cl.$^4$ ............................................. A61C 15/00
[52] U.S. Cl. ........................................ 132/89; 132/91; 132/93
[58] Field of Search ................. 132/84 R, 84 A, 84 B, 132/84 C, 84 D, 85, 89, 90, 91, 92 R, 92 A, 93; 446/374

[56] References Cited

U.S. PATENT DOCUMENTS

| | | | |
|---|---|---|---|
| 407,362 | 7/1889 | Mason | 132/91 |
| 1,414,604 | 5/1922 | Thum | 132/91 |
| 2,522,794 | 9/1950 | Medof | 132/93 |
| 2,931,366 | 4/1960 | Siegel | 132/93 UX |
| 3,999,562 | 12/1976 | Reukauf | 132/89 |
| 4,194,290 | 3/1980 | Vallhonrat | 132/89 |
| 4,280,518 | 7/1981 | Gambaro | 132/93 |
| 4,326,314 | 4/1982 | Moret et al. | 132/84 R |
| 4,403,623 | 9/1983 | Mark | 132/84 R |

FOREIGN PATENT DOCUMENTS 2229381  5/1974  France ................................. 132/89

Primary Examiner—Gene Mancene
Assistant Examiner—Carolyn A. Harrison
Attorney, Agent, or Firm—Stanley W. Sokolowski

[57] ABSTRACT

A sanitary, hygienic dental/oral appliance synergistically combining six functions in one device to conveniently and even disposably provide for complete dental/oral hygiene in a portable package. A complete dental/oral hygiene device comprising a hypotraumatic (non-abrasive), large working/brushing-surface headpiece mounted upon a shaft. The shaft proximal end is adapted for scraping and stain removing. A flexible toothpick mounted upon the shaft as well as a measure of dental floss with a cover to hold the floss in place. Also described as a fibro-cellular (spongy), bristle-free, first absorbent toothbrush, preimpregnated with fluoride gel/toothpaste, combined with a novel "winged toothpick", dental floss, stain scraper & gum/teeth stimulator/vibrator tips, for easy-to-use, economically very pleasant, pain-free, comprehensive & complete dental/oral hygiene program.

6 Claims, 5 Drawing Figures

TOOTHSTICKS "TOOSTIX"

BACKGROUND OF THE INVENTION

The instant invention pertains to dental appliances, and more particularly to personal devices for daily tooth hygiene. "Personal dental hygiene" has in the past referred to toothbrushes, toothpastes/gels, dental floss and toothpicks. The conventional toothpick is a traumatic device for the gums of a user and must be improved upon. Dental floss is only necessary due to the limitations of the toothbrush. The conventional toothbrush is not a perfect device. Like dental floss, it is hard to use. Its working surface versus overall structure is tiny and, therefor, requires dexterous manipulation in order to do a complete job. The very young, and the handicapped, therefor, do not and cannot get the full benefit that may be derived from brushing. A toothbrush is further incapable of conforming to the intricacies of the contours and surfaces of the teeth. It is also abrasive to the enamel and lacks sufficient flexibility making it injurious to soft and tender gum tissue.

It should be further noted that toothbrushes are, relatively, for their working surfaces, and, especially in their electric versions, generally heavy and unwieldy in use.

It is also difficult to maintain sanitary conditions for a regular toothbrush over a period of time.

SUMMARY OF THE INVENTION

It is known that sanitary conditions and their maintenance are an important part of overall mouth hygiene. It has been difficult to maintain sanitary conditions in the past, and the various devices previously used to maintain mouth hygiene have been difficult to store and retrieve, sometimes being misplaced, sometimes being contaminated by their surroundings. The devices have also been difficult to use, had small active working surfaces, tasted bitter or otherwise "bad", were abrasive or otherwise detrimental to mouth tissues, and have not been able to produce a copious amount of "foam" or "foaming action"-which is necessary in order to increase the active state of working cleaners or chemicals many fold, rendering them dramatically more effective, and in a similar manner to vastly increase the surface area of the cleaners for higher penetration into cracks, crevices & contours of the mouth, decreased surface tension which increases the chemicals "anti-sticking" activity on food particles, pigments, plaque material . . . etc., loosening them off and out from between teeth, and finally, to dramatically intensify the sweet or "good" taste of the flavors and essential oils that are added to the chemical cleaners. The same "intensification" of action/s holds true for sensitive teeth and gums soothing-ingredients (e.g. potassium nitrate), tobacco or "tar" stains-lifting ingredients and even so-called "breath freshners" & more vital fluoride action. Disposability would add significantly to the maintenance of sanitary conditions and dental hygiene.

Hence, it is an object of the instant invention to provide a device for dental hygiene which has associated with it, all features of standard dental hygiene as known by the prior art in one single device.

It is a further object of the instant invention to provide a highly inexpensive but nevertheless operationally effective, disposable, complete dental hygiene device. It is still a further object of the instant invention to provide a vibrating device inherent with the other functions of the device.

It is still a further object of the instant invention to provide a portable device that will allow a complete dental hygiene program to be maintained "on the run" such that in-between meals, snacks and sugar-containing drinks which no longer not only need not be limited or eliminated but can now become practical, convenient and fun.

BRIEF DESCRIPTION OF THE DRAWINGS

The invention will now be particularly described namely by way of example, so that other objects, features and advantages thereof, its organization, construction and operation will be best understood from the following detailed description taken in conjunction with the several figures and the accompanying drawings in which.

DESCRIPTION OF THE PREFERRED EMBODIMENT

Figure 1:
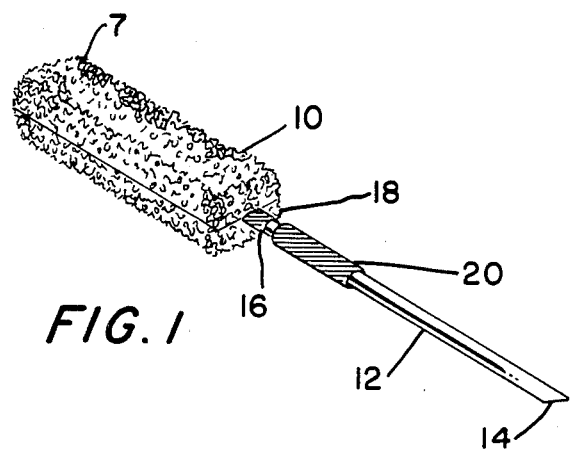
FIG. 1 is a perspective view of the instant invention

Turning to FIG. 1, the synergistic nature of the instant invention is fully displayed, showing the dental hygiene device as it would look "on the market". The main working surfaces are fibro-cellular with "No-Bristles" structure 10 which is preferably "glued" onto a supporting shaft or handle 12 with non-toxic adhesive (not shown). The handle proximal end is equipped with a stain scraper 14 for specifically attacking those hard-to-defeat tooth splotches. Near the preferably open-cell foam structure 10 is wound a measure of dental floss 16 which is held in position under a tape or wax cover 18.

Farther down the handle 12, a novel "winged" toothpick 20 is wound so that it holds itself in place on the handle 12. The handle 12 itself can be made either of wood or plastic and/or metal. Alternatively, a "children's model" may be constructed of paper and/or pulp. Naturally, these are preferred materials and disclosure is not meant to limit. Nor should showing a cylindrical structure be taken as a limiting embodiment.

The foam structure 10 can be impregnated or pre-impregnated with a chemical cleanser (not shown) such as toothpastes or gels. The vast working surface area of the foam 10 compared with the relatively tiny working area of standard toothbrushes allows the instant invention to generate copious cleansing foam immediately upon use. Besides, the "Fibro-cellular design" strongly promotes foam production, in marked contrast to the "non-cellular, bristle design" of the conventional toothbrushes.

Figure 2:
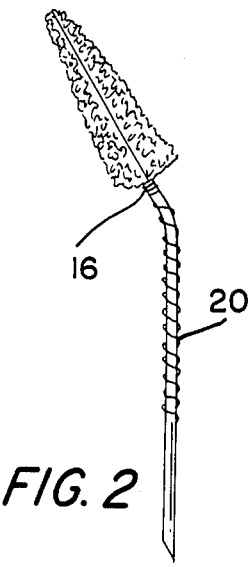
FIG. 2 is a side elevation of a different form of the instant invention

The much greater volume and porosity of foam 10 allows storage and retention of a much greater amount of chemical cleanser on a permanent basis than does a standard toothbrush. Handle 12 is either naturally flexible or "angled" like a dental instrument (see FIG. 2). Handle 12 then does double duty as a vibrator/stimulator, especially when coupled with an electrically-powered holder via special adapter 24.

Figure 3:
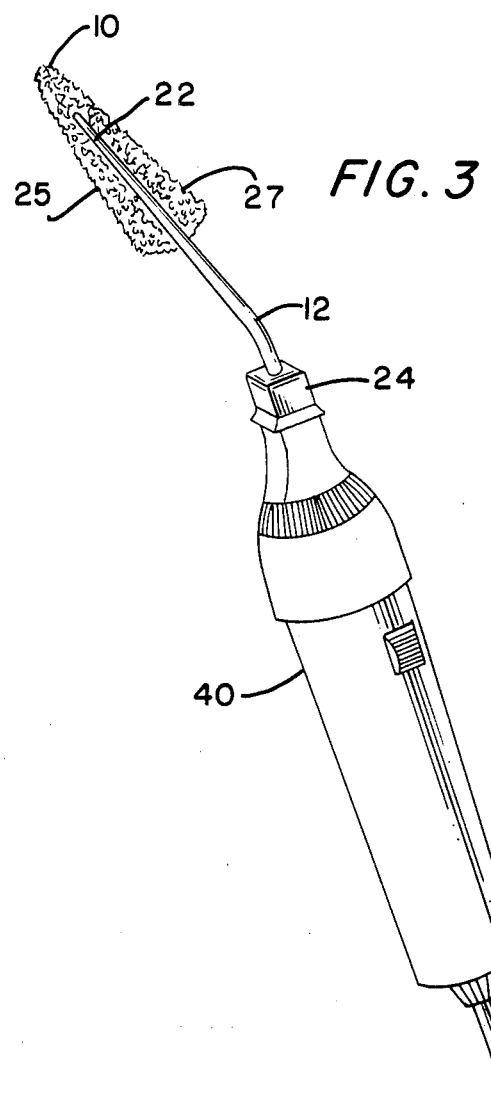
FIG. 3 is a side elevation of the instant invention showing dual major working surfaces and an electric attachment.

The foam structure "head" 10 can be laminated together or onto handle 12. This also allows a multiple grade of foam such as large-cell (firm) 25 and small-cell (soft) 27 to be placed upon one such device. Though FIG. 3 shows only two grades of foam 10, it is understood that many more, not only grades but colors can co-exist on one device.

Figures 4, 5:
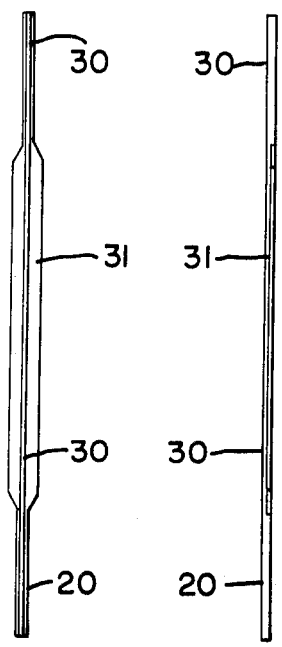
FIG. 4 is a front elevation of a winged, flexible toothpick made after the manner of the instant invention.
FIG. 5 is a side elevation of the pick of FIG. 4

The novel winged toothpick 20 is shown from the front in FIG. 4 and from the side in FIG. 5. The toothpick 20 comprises a central supporting wire 30 covered by flexible plastic 31. The "wings" 31 extend laterally from wire 30 in the central or middle region of toothpick 20 and taper to just cover the wire 30 at the ends & two tips. Toothpick 20 can be much longer than the usual length of prior art picks. Wire 30 may come in multiple gauges for picking particles from between teeth having normal spaces between them to those having extrafine spaces. For those teeth which have grown so close together that there is not enough space to pick them, dental floss 16 is provided under cover 18. Floss 16 is attached at one point to the instant invention, roughly midway on the shaft, allowing handle 12 to make flossing significantly easier as only the loose end 16 need to held by a user's fingers with the other end securely in hand.

So it is seen that the instant invention synergistically combines toothbrush, toothpaste, toothpick, dental floss, stain scraper and dental stimulator/vibrator into one, single "all-encompassing" device. The device can be easily adapted to electric toothbrush holders as well. It should be noted that the all-encompassing device can be manufactured with sufficient industrial economy so as to render it cheap for the ultimate consumer and hence disposable.

In operation, the cleansing process is preferably begun by using the "winged" toothpick 20 to initially remove large food particles from between teeth. It is first unrolled from its storage position (wound around handle 12). One of the two capped wire ends 30 is passed between a chosen and adjacent pair of teeth. Pick 20 is then pushed through until soft & flexible plastic wings 31 are situated therebetween. Pick 20 is then rotated while remaining between the teeth. This then cleans the major areas where food particles stick and begin to ferment/putrify producing acid which cause decay to start at the surrounding tooth surfaces, "Halitosis" (bad breath) and may lead to infections in the mouth cavity or sore throat with dreaded or even deadly complications of "Rheumatic" heart, kidney & nervous system "Korea" diseases. Alternatively, floss 16 may be used for those areas not penetratable by wire 30 of pick 20. Scraper-end 14 of handle 12 may then be used to attack tough or stubborn ugly stains that may be present on a visible surface of tooth enamel. Using a powered holder 40, tip 22 can itself do double-duty as a scraper. Finally, wetted head 10 is inserted into the user's mouth, briskly and vigorously rubbed back and forth across the user's teeth. The entire surface area of head 10 is useful as a working surface, therefor, dexterous and complicated movements are not necessary to get working surfaces to brush the teeth well & completely. This is primarily due the extra-flexibility of the head 10 material, its unique fibro-cellular design and its unusual readiness to "conform" to the toothsurfaces and contours. Tough bristles account for abrasiveness and "non-conformity" of conventional toothbrushes. The pointing in one direction of the bristles, in general, on the other hand accounts for the "almost universal" brushing in a horizontal or "dragging" style considered "improper" or "wrong" by the dental profession. The toothstick, subject of this invention has no bristles, instead it has only soft and/or firm fibers, short, always rounded and pointing in all directions, hence it is immaterial which direction the brushing movements are. Therefor, there is hardly a wrong style in brushing with the toothstick. It can be used in any & in all directions. This makes brushing a much simpler and much more practical task than operations involving prior art brushes which, incidentally, was introduced over 200 years ago with only minor changes since then. It is also a much more effective task as head 10 while not only having 6–8 times greater "active" brushing surface area than prior art brushes, also produces 3 to 4 times greater "foaming action" than do prior art brushes. "Foaming action" is highly important in the cleaning process, because in the "foam state", the cleaning agents themselves are distributed over a huge surface area, possess the lowest surface tension and hence highest "anti-sticking" activity and have the ultimate penetrating power for deep cleaning in cracks and between teeth. Because the instant invention can produce a significantly greater foaming action than can the prior art, it does produce far superior teeth cleaning action & teeth fluoridation as well, which is of paramount importance particularly for children with growing teeth. By pressing the very tip 22 of head 10 against the gums, the instant invention 7 can also be used as a vibrator/gum-stimulator. This is especially true if invention 7 is used in conjunction with an "electric toothbrush" (or battery operated), powered holder 40 via special adapter 24, also for producing superior & extra-fine foam. So, it is seen that the instant invention is a very lightweight, novel-design, heavy duty, six-functions, multigrade, hypotraumatic, nonabrasive, economically disposable, fibrocellular, highly absorbent toothbrush with fluoride gel/toothpaste cleansers pre-impregnated under a vast working surface, with a novel flexible toothpick, dental floss, stain scraper and gum stimulator/vibrator for a complete, easy to use, very pleasant, portable, pain free and comprehensive dental hygiene program for home and "at work" use, strongly recommended for prompt use after meals and all snacks on a regular basis, and easily adaptable to powered holders, while maintaining sanitary conditions for the user.

It will be understood that variations could be made on the embodiment described without departing from the essential features of the invention and the preferred embodiments are not intended to limit the spirit or scope of the invention as set forth in the appended claims, thus I claim:

1. A complete, disposable, dental hygienic instrument, comprising:
   an elongate handle means;
   a resilient, open-cell foam scrubbing and brushing means fastened to a first end of said elongate handle means;
   scraping and stain removing means provided by a generally wedge shaped second end of said elongate handle means;
   dental floss having one end thereof permanently attached to said elongate handle means at a point intermediate the ends of said elongate handle means, the balance of said dental floss is wrapped around said elongate handle means for storage, the other end of said dental floss being unrestrained and free for grasping;

toothpick means removably and conformably wound about said elongate handle means, said toothpick means comprising an elongate malleable wire core completely covered by flexible plastic coating means further projecting laterally into a pair of diametrically opposed thin plastic ribs, said ribs being substantially in the same plane as said wire core and thinner at their distal edge than the coated wire and extending more than a millimeter laterally.

2. The invention of claim 1, wherein said foam brushing and scrubbing means contains dentifrice.

3. The invention of claim 1 wherein the second end of said elongate handle means includes connecting means for connection to powered motion means for mechanically assisted tooth cleaning.

4. The invention of claim 1 wherein said elongate handle means is bent at an angle from the straight to facilitate access to certain regions of the mouth.

5. A toothpick comprising: a central, longitudinal, malleable wire core; a flexible plastic coating means covering said wire core completely along its length and at its ends; two coplanar, diametrically opposed thin, flexible plastic wings coextensive with said plastic coating means, and extending laterally a plurality of millimeters from said wire core along a generally mid-section area of said wire core.

6. The device of claim 5, wherein:
the leading and trailing edges of said wings taper to the central wire coating.

* * * * *